(12) United States Patent
Song et al.

(10) Patent No.: US 6,723,337 B1
(45) Date of Patent: Apr. 20, 2004

(54) TRANSDERMAL DRUG DELIVERY SYSTEM FOR ANTI-INFLAMMATORY ANALGESIC AGENT COMPRISING DICLOFENAC DIETHYLAMMONIUM SALT, AND THE MANUFACTURING METHOD THEREOF

(75) Inventors: Jin Deog Song, Daejeon (KR); Chul Min Park, Daejeon (KR); Young Kwon Choi, Daejeon (KR); Heon Han Lee, Daejeon (KR); Yong Ho Shim, Daejeon (KR); Hye Jeong Yoon, Daejeon (KR)

(73) Assignee: Samyang Corporation, Seoul (KR)

(*) Notice: Subject to any disclaimer, the term of this patent is extended or adjusted under 35 U.S.C. 154(b) by 0 days.

(21) Appl. No.: 09/509,303

(22) PCT Filed: Sep. 25, 1998

(86) PCT No.: PCT/KR98/00295

§ 371 (c)(1),
(2), (4) Date: Jun. 19, 2000

(87) PCT Pub. No.: WO99/16434

PCT Pub. Date: Apr. 8, 1999

(30) Foreign Application Priority Data

Sep. 26, 1997 (KR) .......................... 1997/49084

(51) Int. Cl.[7] .......................... A61F 13/02; A61F 13/00; A61F 15/16; A61K 9/14
(52) U.S. Cl. .................. 424/448; 424/443; 424/447; 424/449; 424/484; 424/486; 424/487; 516/946; 516/947; 516/964
(58) Field of Search .................. 424/449, 443, 424/447, 448, 484, 486, 487; 514/946, 947, 964

(56) References Cited

U.S. PATENT DOCUMENTS

| 4,537,776 A | 8/1985 | Cooper |
| 4,738,848 A | 4/1988 | Yoshida et al. |
| 4,999,379 A | 3/1991 | Fankhauser |
| 5,176,916 A | * 1/1993 | Yamanaka et al. .......... 424/448 |
| 5,208,035 A | 5/1993 | Okuyama et al. |
| 5,350,769 A | 9/1994 | Kasai et al. |
| 5,422,102 A | 6/1995 | Ikeda et al. |
| 5,429,590 A | * 7/1995 | Saito et al. ................... 602/48 |
| 5,607,690 A | 3/1997 | Akazawa |
| 5,641,504 A | * 6/1997 | Lee et al. ................... 424/447 |

FOREIGN PATENT DOCUMENTS

| EP | 0 428 352 A1 | 11/1990 |
| EP | 0 524 582 A1 | 7/1992 |
| EP | 0 581 587 A2 | 7/1993 |
| EP | 0 600 395 A1 | 11/1993 |
| EP | 0682942 | * 11/1995 |
| GB | 2192539 | * 1/1988 |
| JP | 4193826 | 7/1992 |
| WO | WO 92/20377 | 11/1992 |

* cited by examiner

Primary Examiner—Michael G. Hartley
Assistant Examiner—Sharmila S Gollamudi
(74) Attorney, Agent, or Firm—Thorpe North & Western, LLP

(57) ABSTRACT

The invention herein relates to a transdermal drug delivery system for anti-Inflammatory analgesic. agent comprising diclofenac diethylammonium salt, wherein a backing film (1), a matrix layer (2) containing active ingredients, a release liner (3) which is removed before application onto the skin are laminated therein. Mome particularly, the invention herein relates to a transdermal drug delivery system for anti-inflammatory analgesic agent comprising diclofenac diethylammonum salt, wherein the transdermal penetration and adhesion of the patch to the body are enhanced by means of a matrix layer which comprises a diclofenac diethylammonum salt as active ingredient in addition to acrylic polymer as adhesive constituent, non-ionic surfacant as absorption enhancer, terpene and dissolution assistant, and the volatile and non-volatile constituents of the composition arc separately applied therein for significantly reducing the manufacturing time thereof.

9 Claims, 4 Drawing Sheets

TRANSDERMAL DRUG DELIVERY SYSTEM FOR ANTI-INFLAMMATORY ANALGESIC AGENT COMPRISING DICLOFENAC DIETHYLAMMONIUM SALT, AND THE MANUFACTURING METHOD THEREOF

BACKGROUND OF THE INVENTION

This application is a 371 of PCT/KR 98/00295, filed Sep. 25, 1998.

1. Field of the Invention

The invention herein relates to a transdermal drug delivery system for anti-inflamnatory analgesic agent comprising diclofenac diethylammonium salt, wherein a backing film, a matrix containing active ingredients, a release liner which is removed before application onto the skin are laminated therein. More particularly, the invention herein relates to a transdermal drug delivery system for anti-inflammatory analgesic agent comprising diclofenac diethylammonium salt, wherein the transdermal penetration and adhesion of the patch to the body are enhanced by means of a matrix layer which comprises a diclofenac diethylamnmoniun salt as active ingredient in addition to non-aqueous acrylic polymer as adhesive constituent, non-ionic surfactant as absorption enhancer, terpene and dissolution assistant, and the volatile and non-volatile constituents of the composition are separately applied therein for significantly reducing the manufacturing time thereof.

2. Description of the Prior Art

Diclofenac salt, one of non-steroid anti-inflammatory drugs (NSAIDs), shows therapeutic efficacy by means of inhibiting a biochemical reaction path which is necessary for the biosynthesis of a pain inducer, prostaglandin. Diclofenac is a drug which has the effects of pain relief, antifebrile and anti-inflammation and is widely applicable in rheumatic arthritis, osteoarthritis, spastic spondylitis, acute gout, and inflammation or gout of lesion after operation. However, if diclofenac is orally administered for a long period of time, a peptic ulcer is induced along with other side effects such as anemia by hemorrhage. In order to reduce such side effects on stomach, which is most problematic for an oral dosage form, a research into the method of formulating the same into a transdermal administration matrix has actively been in progress. In general, the subject matters of the research done thus far can be classified into a topical dosage form and a patch (transdermal drug delivery system).

The prior art relating to the topical dosage form is disclosed in U.S. Pat. Nos. 4,537,776. 5,350,769, 5,422,102, and European Unexamined Patent No. 0,428,352 A1 and International Unexamined Patent No. WO 92/20377. The aforementioned prior art relates mainly to get, emulsion and ointment, which are directly applied onto the skin without a backing film for sealinrg the active ingredients. As such, the topical dosage is inconvenient in that the pharmaceutical composition may smear on clothe, result in variable application dosage, emit odor and necessitate a multiple daily application.

On the other hand, a patch has a constant dosage for application without the inconvenience of smearing on clothe or multiple applications. A patch can generally be classified into reservoir and matrix types. As for the reservoir type, the pharmaceutical composition of gel, emulsion or ointment can be used but cannot be applied to joints and curved body parts. On the other hand, a matrix type is convenient in that it can be applied to anywhere on the body depending on the properties of a backing film and adhesive constituent. Although the matrix can be applied to the skin for a long period of time without irritation, a difficulty arises in the system architecture in that an absorption enhancer must be added in order to maintain a continuous transdermal penetration.

With respect to the patch of a matrix type, for enhancing the transdermal penetration, U.S. Pat. No. 4,738,848 used diclofenac in a free acid form converted from sodium diclofenac salt via such organic acids as citric acid. In Korean Unexamined Patent No. 94-23471, the transdermal penetration of the accumulated diclofenac was increased to 180 $\mu$g/cm$^2$·day by using a composition comprising hydroxy ethyl pyrrolidone or hydroxy ethyl piperidine as absorption enhancer.

Further. Korean Unexamined Patent No. 93-1896 disclosed a sodium diclofenac salt plaster comprising an absorption enhancer of menthol and propylene glycol, and a hydrophilic substrate having a water-soluble polymer. In the aforementioned prior art, the examples of water-soluble polymers generally used in the plaster as substrate constituents include polyacrylic acid, sodium polyacrylate, carboxyvinyl polymer, sodium carboxymethyl cellulose, polyvinyl pyrrolidone, polyvinyl alcohol and gelatin. The solid part of the plaster, comprising the water-soluble polymer as main substrate, moisturizer, humectant lysosome, inorganic filler, viscosity controller, cross-linking agent, active ingredient, was manufactured by a process of mixing of the combinants, stirring and then surface application. However, if the surface application of all the pharmaceutical compositions is carried out at once with the plaster containing volatile menthol and propylene glycol, the prolong drying process at a low temperature range of 40~50° C. was necessary after application. Further, in the case of such solid plaster, it was too thick to the point that adhesion sensation was unduly excessive with poor adhesion, which in turn resulted in easy detachment.

SUMMARY OF THE INVETION

The invention herein uses diclofenac diethylanimonium salt as active ingredient and non-aqueous acrylic polymer with superior solubility in organic solvents instead of a water-soluble adhesive constituent. In order to increase absorption, the invention includes a non-ionic surfactant and terpene at a certain mixing ratio. For increasing the drug concentration, the invention includes a dissolution assistant in a certain amount so that the transderrnal drug delivery of the active ingredient is more than doubled as compared to Korean Unexamined Patent No. 94-23741. Therefore, the objective of the invention herein is to provide a transdermal drug delivery system comprising diclofenac diethylanunonium salt, wherein the transdermal drug delivery of the active ingredient is more than far more superior than that of the prior art without undue deterioration of adhesion to the body even for a long-term application.

Further, as for the matrix layer of the present invention, unlike other plasters of the prior art, the adhesive layer (2a') is formed by applying a non-volatile constituent among the total pharmaceutical composition onto one side of the backing film, after which is dried for a short period time at a high temperature. Thereafter, a volatile absorption enhancer layer (2b) is formed by separately applying volatile constituents comprising a dissolution assistant and a compound such as terpene for imparting cool sensation upon initial application to the body. Another adhesive layer (2a") is formed onto the release liner (3) by the aforementioned method, after which is laminated onto the upper portion of the volatile absorption enhancer layer (2b), thereby forming the matrix layer (2) herein. Consequently, another objective of the present invention lies in providing a manufacturing method of a transdermal drug delivery system having diclofenac diethylammonium salt, wherein the manufacturing time is significantly reduced.

BRIEF DESCRIPTION OF THE DRAWING

In FIG. 1, (1) as indicated is a backing film. (2) is a matrix layer containing active ingredients. The matrix layer includes two adhesive layers containing non-volatile constituents, which are indicated by 2a' and 2a". Within the matrix layer, there is another layer 2b containing volatile constituents, which is denoted as absorption enhancer. Lastly, (3) indicates a release liner of the transdermal drug delivery system.

DETAILED DESCRIPTION OF THE INVENTION

Figure 1:
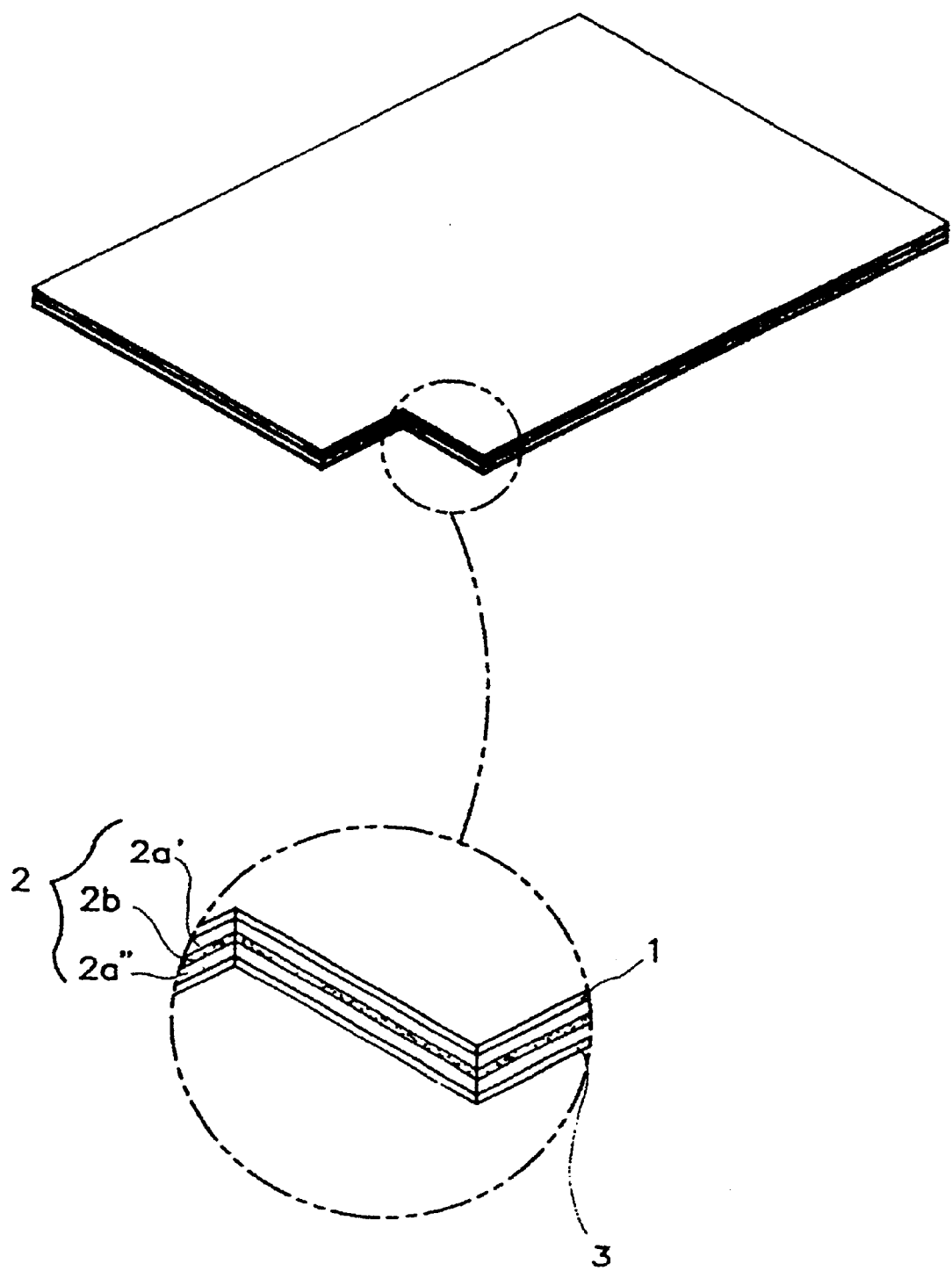
FIG. 1 is a cross-sectional view of the transdermal drug delivery system.
Figure 2:
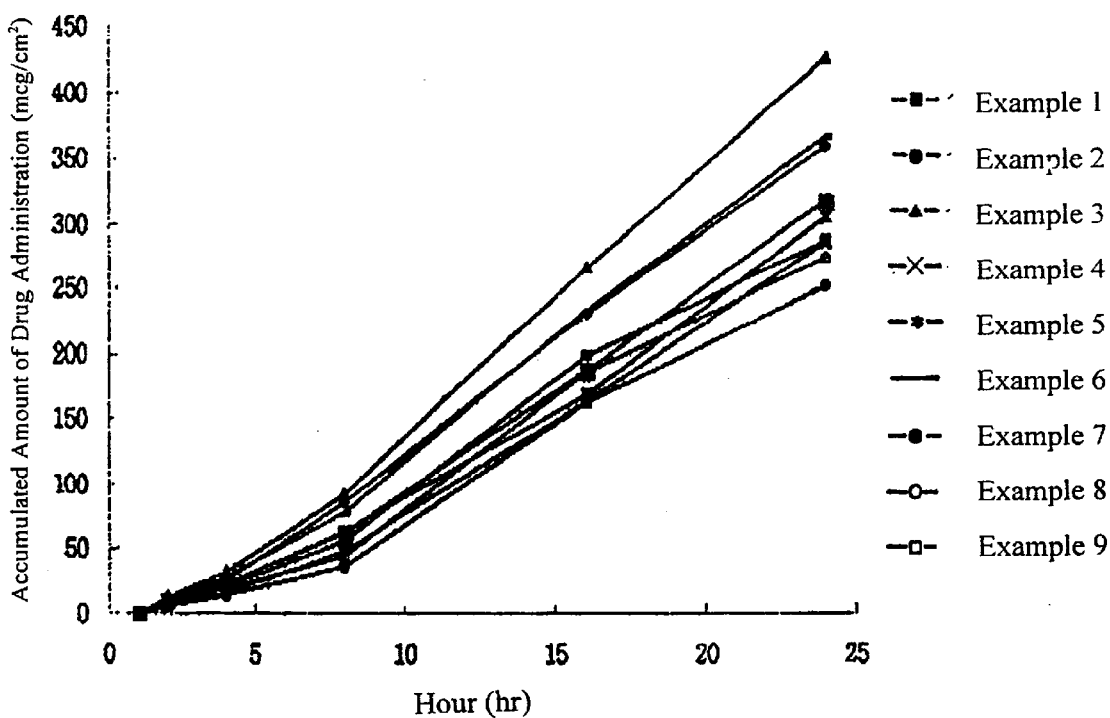
FIG. 2 is a graph showing the accumulated amounts of the penetrated active ingredients for examples 1~9.
Figure 3:
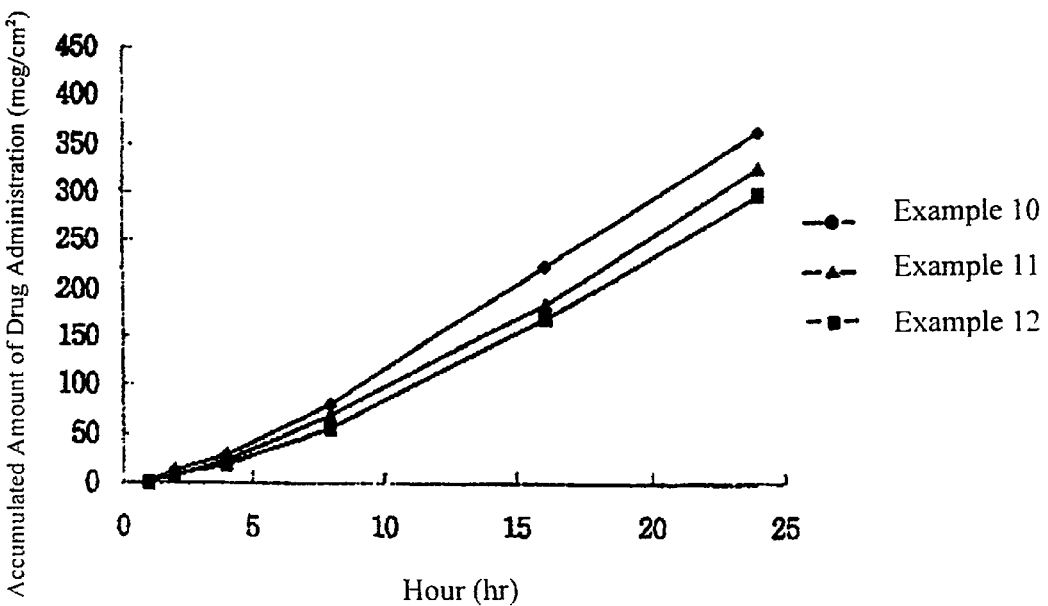
FIG. 3 is a graph showing the accumulated amounts of the penetrated active ingredients for examples 10~12.
Figure 4:
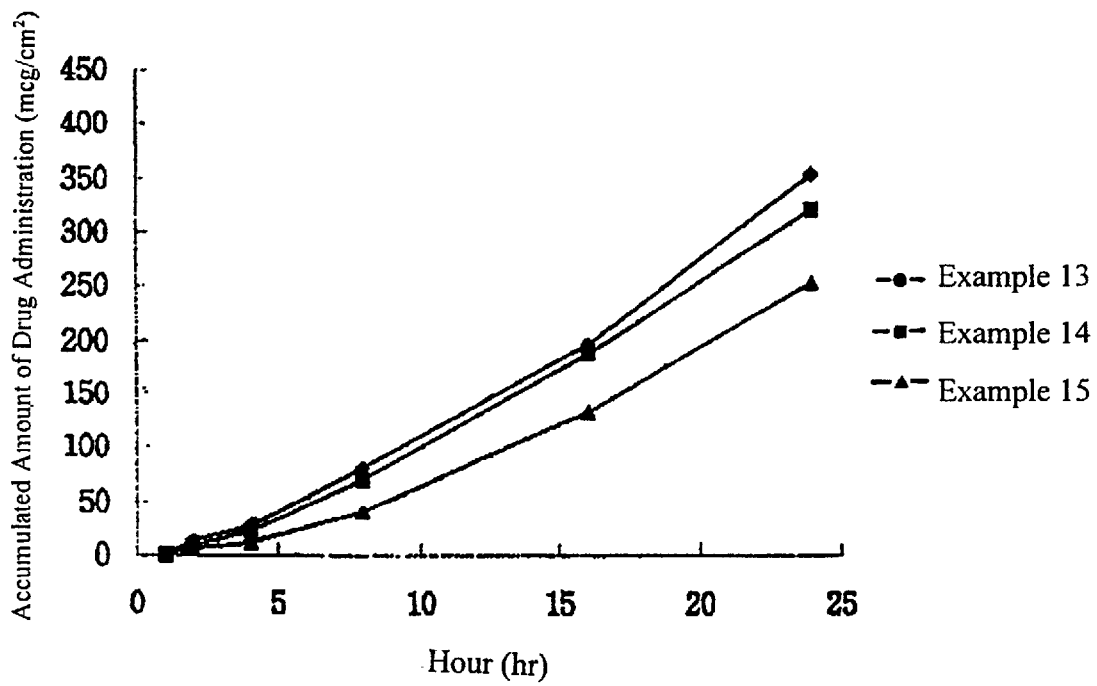
FIG. 4 is a graph showing the accumulated amounts of the penetrated active ingredients for examples 13~15.
Figure 5:
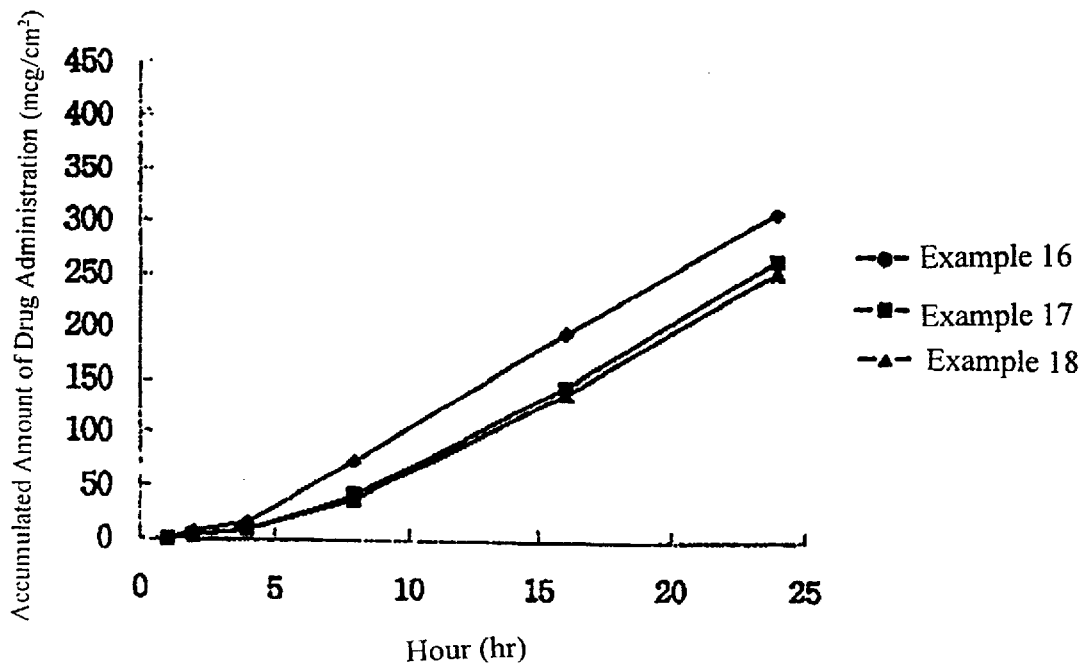
FIG. 5 is a graph showing the accumulated amounts of the penetrated active ingredients for examples 16~18.
Figure 6:
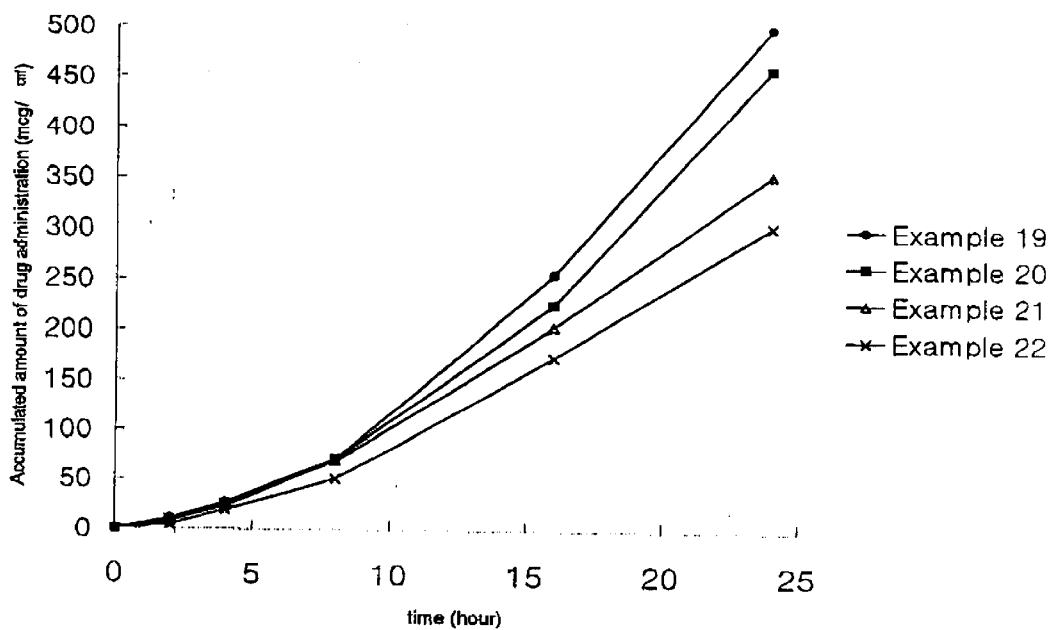
FIG. 6 is a graph showing the accumulated amounts of the penetrated active ingredients for examples 19~22.
Figure 7:
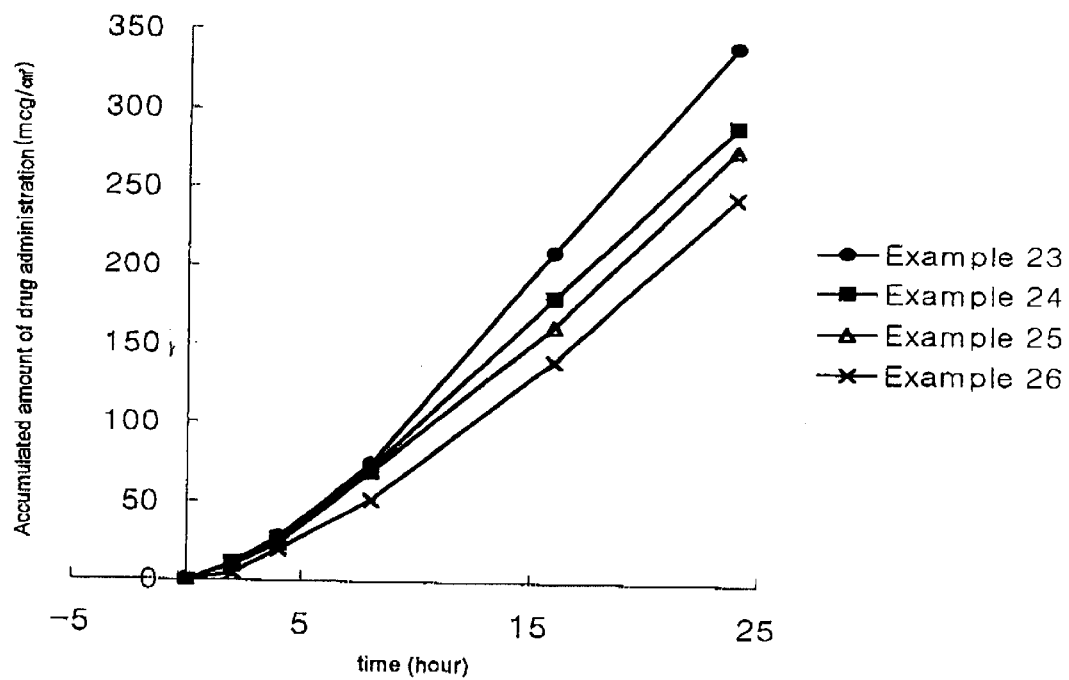
FIG. 7 is a graph showing the accumulated amounts of the penetrated active ingredients for examples 23~26.

A transdermal drug delivery system of the present invention comprises a backing film (1), a matrix layer (2) having active ingredients, a release liner (3) which is removed before application onto the skin. In particular, the matrix layer (2) comprises 1~25weight % (wt %) of diclofenac diethylammonium salt as active ingredient. 40~95 wt % of non-aqueous acrylic polymer as adhesive constituent, 0.1~20 wt % of non-ionic surfactant, 0.1~10 wt % of terpene, and 0.1~10 wt % of dissolution assistant.

The invention herein is described in more detail as follows: The invention uses a non-aqueous acrylic polymer having superior adhesion and durability instead of a water-soluble polymer as adhesive constituent, which is generally used in the plaster. Consequently, the amount of the adhesive constituent is reduced, thereby significantly decreasing the thickness of the patch. The invention is not only applicable on the flat areas of the body but also on the curved parts for a long period of time with relatively comfortable feeling on application. Further, a non-ionic swUfactant and terpene at a certain mixing ratio are used as absorption enhancers, In order to increase the concentration of the drug within the patch, a dissolution assistant is used, thereby resulting in a synergic effect of the transdermal drug delivery of diclofenac diethylammonium salt in addition to significantly increasing the administration dosage of the active ingredient.

In the present invention, it is appropriate to include an active ingredient in the amount of 1~25 wt % of diclofenac diethylammonium salt to the total composition within the matrix layer. If the amount of an active ingredient is less than 1 wt %, the transdermal absorption is significantly reduced due to a reduction in the drug concentration. On the other hand if the amount is more than 25 wt %, the active ingredient within the patch is extracted out from the matrix layer due to the insufficient solubility thereof.

In addition, for increasing the concentration of the active ingredient within the matrix, the invention uses a non-aqueous acrylic polymer as adhesive constituent, which has high solubility in organic compounds and superior adhesion as compared to the water-soluble polymer. As such, the matrix layer is thin with high concentration of the active ingredient within the patch. Then, the transdermal absorption is increased thereby, which in turn results in superior adhesion, for long-term application onto the skin. Further, due to the thin adhesive layer containing the active ingredient, the drying process of the adhesive layer in a short period of time is achieved, which in turn has the effect of significantly reducing the manufacturing time. As for the adhesion constituent, non-aqueous acrylic polymers such as pressure sensitive adhesive is selected, which is included in the amount of 40~95 wt % to the total composition of the matrix layer. If the amount of the adhesion constituent is less than 40 wt %, the matrix layer is formed without appropriate epidermal adhesion. If it is more than 95 wt %, the matrix cannot support the active amounts of the active ingredient, absorption enhancer and dissolution assistant. The non-aqueous acrylic polymer used as adhesion constituent may include acrylate polymer, or a co-polymer of acrylate and vinylacetate with or without carboxyl (—COOH) and hydroxyl (—OH) functional groups.

In addition, a non-ionic surfactant and terpene are used as absorption enhancers. The absorption enhancer increases the absorption of the active ingredient on the skin, in a manner directly proportional to the dosage amount, to a certain point of the concentration. However, the absorption enhancer at or above such point of the concentration tends to irritate the skin instead of enhancing the absorption, With this in mind, the absorption enhancer is used within the appropriate range of concentration.

As for the non-ionic surfactant, one or more is selected from the group consisting of glyceryl mono-oleate, glyceryl mono-laurate, sorbitan mono-oleate, glyceryl tri-oleate, and isopropyl myristate. The non-ionic surfactant is used in the amount of 0.1~20 wt % to the total composition of the matrix layer.

A terpene is selected from the group consisting of menthol, D-limonene, geramol and nerolidol and included in the total composition of the matrix layer at 0.1~10 wt % thereof.

Further, a dissolution assistant is added herein to increase the concentration of the active ingredient within the matrix layer. As for the dissolution assistant, one or more is selected from the group consisting of triacetin, isopropyl alcohol, propylene glycol, dimethylacetamide, propylene carbonate, diethylethanolanine, diethyl amine, triethylarnine, N-methyl morphorine and benzyamrnonium chloride, which is added in the amount of 0.1~10 wt % to the total composition of the matrix layer.

With respect to the combination of the non-ionic surfactant, terpene and dissolution assistant, the following combinations show superior transdermal penetration: glyceryl mono-oleate/menthol/propylene glycol; glycerine mono-laurate/menthol/propylene glycol; sorbitan mono-oleate/menthol/triacetin, isopropyl alcohol; sorbitan mono-oleate/menthol/propylene glycol; glyceryl mono-laurate/menthol/triacetin.

Further, a gelling polymer may be added in addition to the aforementioned constituents of the matrix layer. As for the gelling polymer, hydroxy propyl cellulose, hydroxy methyl cellulose, carbomer and other commonly used gelling polymers may be used herein. It is added in the amount of less than 5 wt % to the composition constituent of the matrix layer.

The composition constituent of the matrix layer of the present invention comprises preferably 1~20 wt % of diclofenac dimethylammonium salt, 40~95% of non-aqueous acrylic polymer adhesive agent, 1~15 wt % of sorbitan mono-oleate, 0.1~5%wt % of menthol, 0.1~5 wt % of triacetin, isopropyl alcohol or propylene glycol as dissolution assistants and 0~1 wt % of gelling polymer. The transdermal drug delivery system as such are shown to have superior transdermal penetration and adhesion.

Further, the conventional plaster containing a water-soluble polymer had poor adhesion for application onto the curved body parts for a long period of time due to the thick adhesive layer. Being water-soluble, the conventional plaster showed limitation with respect to supporting a large amount of active ingredients due to poor solubility of drug for water. On the other hand, the present invention uses a non-aqueous acrylic polymer instead of a water-soluble polymer of the prior art for the purpose of dissolving the active ingredients at high concentration, and consequently a relatively thin adhesive layer of less than 300 µm is incorporated into the matrix layer.

With respect to the manufacture of the transdermal drug delivery system of the present invention, a backing film is a non-woven fabric or film comprising polymer substrates selected from the group consisting of polyurethane, polyester, polyethylene and rayon. As for the release liner, a disposable film impermeable to drugs which is commonly used in the manufacture of the patch is utilized, FIG. 1 is a cross-sectional view of the transdermal drug delivery system containing diclofenac diethylammonium salt, The transdermal drug delivery system of the present invention comprises a backing film (1), a matrix layer containing active ingredients, and a release liner (3) which is removed before the application onto the skin. Onto the matrix layer (2) containing active ingredients, the adhesive layers (2a', 2a") having diclofenac diethyammonium salt and non-volatile constituents are laminated into two layers. Between the two adhesive layers (2a', 2a"), the absorption enhancer layer (2b) comprising such volatile constituents as volatile absorption enhancers and dissolution assistants are inserted therein. In the case of the adhesive layer (2a') adjacent to the backing film (1), it is possible to manufactured the same by use of an adhesive agent only.

Further, the present invention is characterized by the manufacturing method of the transdermal drug delivery system in that the volatile and non-volatile constituents are separately applied thereto for the formation of the matrix layer (1) instead of simultaneous application of the pharmaceutical compositions. In other words, of all the pharmaceutical compositions, only the non-volatile constituents are selected and applied onto one side of the backing film (1) and the release liner (3). Thereafter, the adhesion layers (2a', 2a") are formed by drying the same at a high temperature range of 80~120° C. for a short period of time of 1~10 minutes. Then, onto the dried adhesive layer (2a'), a high viscosity solution containing volatile constituents is applied, which is seeped onto the adhesive layer at a room temperature, thereby forming the volatile absorption enhancer layer (2b). Then, onto the upper portion of the volatile absorption enhancer layer (2b), the adhesive layer (2a") is once again laminated therein for the purpose of manufacturing the transdermal drug delivery system. Based on the aforementioned process, the drying time for the matrix layer (2) is significantly reduced while suppressing the volatilizing of the volatile constituents by means of an appropriate drying process after application. Further, the manufacturing process herein lacks complicated manufacturing process as compared to the manufacture of a plaster and also works to enhance the wear and adhesion of the trrnsdermal drug delivery system upon application onto the body.

The invention herein is explained in more detail by the following examples but is not limited bv such examples.

EXAMPLES 1~26

A transdermal drug delivery system was manufactured according to the following method, and composition of the matrix layer (2) are shown in Tables 1~6.

Into a 30 ml sample bottle, acrylate adhesive agents (National Starch & Duro-tak™ 87-2852, 87-2196, 87-4098) were placed. After adding diclofenac diethylammonium salt (DDA), it was stirred at 300 rpm until the pharmaceutical compositions were completely dissolved in an adhesion solution. Then, a non-ionic surfactant was added to the adhesion solution, and it was stirred at 300 rpm for mixing of all the constituents in the sample bottle, after which was allowed to stand for 20 minutes. Thereafter, a lab coater and dryer (Mathis Co. of Switzerland) were used to cast the mixture onto the release liner film (3M Scotchpak® 1022) and dried at a high temperature range of 80~120° C. for 10 minutes. The backing film (1) as in FIG. 1 and the adhesive layer (2a') containing pharmaceutical compositions were formed by laminating the aforementioned mixture onto a backing film (3M® non-woven polyurethane 9905, 3M® spun-laced non-woven polyester 1538, 3M® rayon non-woven 1533, 3M® rayon acetate).

On top of the release liner film (3M Scotchpak® 1022, 3M® paper release liner 1361, 9743), another adhesive layer (2a") was formed by the same method as used in the aforementioned adhesive layer (2a'). Then, an adhesion solution was prepared by mixing the solution of terpene and dissolution assistants in addition to a small amount of gelling polymer as deemed necessary. The volatile absorption enhancer layer (2b) was formed by directly dispersing an appropriate amount of the mixture or coating the same onto the dried adhesive layer (2a") via nozzle. By means of dispersing via coating method, the impregnation of an appropriate amounts of terpene and dissolution assistant into the adhesive constituent was possible. The impregnated amount of the mixture solution was appropriately controlled by means of duly manipulating the dispersing time, metering pump speed, and nozzle size.

A transdermal drug delivery system was manufactured by laminating the adhesive layer (2a") and the backing film (1), which had been prepared as composition constituents during the formation of the aforementioned adhesive layer (2a"), onto the upper portion of the dried volatile absorption enhancer layer (2b).

The drug penetration tests of the respective transdermal drug delivery system manufactured as aforementioned were carried out in a phosphate culture (0.05M, pH 7.4) with respect to the skin of the 6-week-old hairless mouse after removing subcutaneous fat by means of the Franz cell automation extraction equipment (Hanson Research Co. of USA). The collected samples were analyzed by 1100 HPLC (Hewlett-Packard Co. of USA), and the results therefrom as classified into 6 separate groups are shown herein.

A transdermal drug delivery system according to the present invention is characterized by a transdermal penetration agents comprising terpene, surfactant and dissolution assistant, which show enhancement effects when the aforementioned constituents are simultaneously utilized. In order to show the amounts of the drug penetration according to the types of the transdermal penetration agent, amounts and composition ratios, the appropriate tests were carried out based on the compositions in the Table 1~6. More specifically, the tests were carried out with respect to menthol propylene glycol, glycerine, isopropyl alcohol, triacetin, glyceryl mono-oleate, glyceryl mono-lureate and sorbitan mono-oleate, which particularly showed superior compatibility and synergistic effects when used simultaneously. The penetration amounts of the accumulated active ingredients of the respective groups are shown in FIGS. 2~7. From the Figures, it was observed that the penetration effect was significantly enhanced based on a small change in the amount of the transdermal penetration agent by means of a synergistic effect due to the mutual action thereof. It was also observed that the penetration amount of the diclofenac diethylammonium salt was enhanced in a more significant manner as compared to other conventional agents.

TABLE 1

| | Composition constituent of matrix layer (wt %) | | | | | | |
|---|---|---|---|---|---|---|---|
| | Drug Diclofenac | Adhesive | Other constituents (absorption enhancer, dissolution assistant, gelling polymer) | | | | Amount |
| Type | Diethyl-ammonium salt | Agent DT 87-2852 | Menthol | Propylene glycol | Glyceryl Mono-Oleate | Hydroxy-Propyl Cellulose | of drug penetration ($\mu$g/cm$^2$ · day) |
| Example 1 | 19.6 | 68.8 | 1.2 | 1.2 | 9.1 | 0.1 | 318 |
| Example 2 | 18.9 | 68.1 | 2.1 | 2.1 | 8.7 | 0.1 | 359 |
| Example 3 | 19.0 | 66.4 | 3.2 | 3.3 | 7.9 | 0.2 | 425 |
| Example 4 | 10.3 | 79.4 | 1.1 | 1.1 | 8.0 | 0.1 | 285 |
| Example 5 | 10.7 | 76.1 | 2.3 | 2.3 | 8.5 | 0.1 | 305 |
| Example 6 | 10.9 | 74.5 | 3.1 | 3.1 | 8.2 | 0.2 | 367 |
| Example 7 | 5.0 | 84.6 | 1.2 | 1.2 | 7.9 | 0.1 | 252 |
| Example 8 | 5.2 | 82.6 | 2.1 | 2.1 | 7.9 | 0.1 | 273 |
| Example 9 | 5.1 | 79.8 | 3.3 | 3.3 | 8.3 | 0.2 | 287 |

TABLE 2

| | Composition constituent of matrix layer (wt %) | | | | | | |
|---|---|---|---|---|---|---|---|
| | Drug Diclofenac | Adhesive | Other constituents (absorption enhancer, dissolution assistant, gelling polymer) | | | | Amount |
| Type | Diethyl-ammonium salt | Agent DT 87-2852 | Menthol | Glycerine | Glyceryl Mono-Oleate | Hydroxy-Propyl Cellulose | of drug penetration ($\mu$g/cm$^2$ · day) |
| Example 10 | 18.7 | 67.0 | 3.3 | 3.3 | 7.5 | 0.2 | 365 |
| Example 11 | 10.5 | 74.8 | 3.4 | 3.4 | 7.7 | 0.2 | 326 |
| Example 12 | 5.7 | 80.1 | 3.1 | 3.1 | 7.8 | 0.2 | 298 |

TABLE 3

| | Composition constituent of matrix layer (wt %) | | | | | | |
|---|---|---|---|---|---|---|---|
| | Drug Diclofenac | Adhesive | Other constituents (absorption enhancer, dissolution assistant, gelling polymer) | | | | Amount |
| Type | Diethyl-ammonium salt | Agent DT 87-2852 | Menthol | Propylene glycol | Glyceryl Mono-Oleate | Hydroxy-Propyl Cellulose | of drug penetration ($\mu$g/cm$^2$ · day) |
| Example 13 | 17.9 | 67.9 | 3.5 | 3.3 | 7.2 | 0.2 | 356 |
| Example 14 | 10.4 | 75.1 | 3.4 | 3.4 | 7.5 | 0.2 | 323 |
| Example 15 | 5.5 | 80.0 | 3.1 | 3.1 | 8.1 | 0.2 | 257 |

TABLE 4

| | Composition constituent of matrix layer (wt %) | | | | | | |
|---|---|---|---|---|---|---|---|
| | Drug Diclofenac | Adhesive | Other constituents (absorption enhancer, dissolution assistant, gelling polymer) | | | | Amount |
| | Diethyl- | Agent | | | Glyceryl | Hydroxy- | of drug |

| Type | ammonium salt | DT 87-2852 | Menthol | Glycerine | Mono-Oleate | Propyl Cellulose | penetration ($\mu g/cm^2 \cdot day$) |
|---|---|---|---|---|---|---|---|
| Example 16 | 18.3 | 67.6 | 3.2 | 3.2 | 7.5 | 0.2 | 312 |
| Example 17 | 10.6 | 74.3 | 3.4 | 3.4 | 8.1 | 0.2 | 267 |
| Example 18 | 5.2 | 79.7 | 3.1 | 3.1 | 8.7 | 0.2 | 256 |

TABLE 5

| | Composition constituent of matrix layer (wt %) | | | | | | | |
|---|---|---|---|---|---|---|---|---|
| | Drug Diclofenac | Adhesive | Other constituents (absorption enhancer, dissolution assistant, gelling polymer) | | | | | Amount |
| Type | Diethyl-ammonium salt | Agent DT 87-4098 | Menthol | Triacetin | Iso-Propyl Alcohol | Sorbitan Mono-Oleate | Hydroxy-Propyl Cellulose | of drug penetration ($\mu g/cm^2 \cdot day$) |
| Example 19 | 17.2 | 68.6 | 2.6 | 1.3 | 1.3 | 8.9 | 0.2 | 483 |
| Example 20 | 12.0 | 73.1 | 2.6 | 1.3 | 1.3 | 9.7 | 0 | 442 |
| Example 21 | 9.6 | 77.0 | 1.4 | 0.7 | 0.7 | 10.6 | 0 | 350 |
| Example 22 | 5.6 | 80.2 | 2.6 | 1.3 | 1.3 | 8.8 | 0.2 | 300 |

TABLE 6

| | Composition constituent of matrix layer (wt %) | | | | | | | |
|---|---|---|---|---|---|---|---|---|
| | Drug Diclofenac | Adhesive | Other constituents (absorption enhancer, Dissolution assistant, gelling polymer) | | | | | Amount |
| Type | Diethyl-Ammonium salt | Agent DT 87-2196 | Menthol | Triacetin | Iso-propyl Alcohol | Sorbitan Mono-Oleate | Hydroxy-Propyl Cellulose | of drug penetration ($\mu g/cm^2 \cdot day$) |
| Example 23 | 18.0 | 67.2 | 3.2 | 1.3 | 10.1 | 10.1 | 0.2 | 331 |
| Example 24 | 11.2 | 72.7 | 3.3 | 1.6 | 11.2 | 11.2 | 0 | 280 |
| Example 25 | 8.5 | 75.6 | 2.2 | 2.2 | 11.3 | 11.3 | 0.2 | 273 |
| Example 26 | 5.6 | 80.7 | 2.3 | 1.3 | 10.1 | 10.1 | 0 | 245 |

As shown above, the transdermal drug delivery system according to the present invention was manufactured by coating the film (2b) containing volatile absorption enhancers and dissolution assistant between the dried adhesive layers (2a', 2a'') containing diclofenac diethylammonium salt and non-volatile absorption enhancer. Further, in order to enhance the transdermal penetration of the active ingredient, the invention uses adhesive constituents with superior adhesion property while including volatile and non-volatile absorption enhancers and dissolution assistant at a certain mixing ratio by means of the aforementioned method. Therefore, the invention has the effects of increasing the transdermal penetration of the active ingredients, enhancing the wear and adhesion onto the curved body parts, and significantly reducing the manufacturing time thereof.

What is claimed is:

1. A transdermal drug delivery system for an anti-inflammatory analgesic agent comprising a backing film, a laminated matrix less than 300 μm in thickness and a release liner; wherein said laminated matrix comprises a volatile layer consisting essentially of 0.1 to 10 wt % of a terpene enhancer and 0.1 to 10 wt % of a dissolution assistant, wherein said volatile layer is sandwiched between two non volatile layers consisting essentially of 40~95 wt % of a non-aqueous acrylic polymer adhesive, 1~25 wt % of diclofenac diethylammonium and 0.1 to 20 wt % of a non-ionic surfactant.

2. The transdermal drug delivery system according to claim 1, wherein said non-aqueous acrylic polymer comprises an acrylate polymer or a co-polymer of acrylate and vinyl acetate.

3. The transdermal drug delivery system according to claim 1, wherein said non-ionic surfactant is selected from the group consisting of glyceryl mono-oleate, glyceryl mono-laureate, sorbitan mono-oleate, glyceryl tri-oleate and mixtures thereof.

4. The transderrnal drug delivery system according to claim 1, wherein said terpene is selected from the group consisting of menthol, d-limonene, geraniol and nerolidol.

5. The transdermal drug delivery system according to claim 1, wherein said dissolution assistant is selected from the group consisting of triacetin, isopropyl alcohol, propylene glycol, dimethylacetarnide, propylenecarbonate, diethylethanolamine, diethylamine, triethylamine, N-methyl morphorine, benzylammonium chloride, isopropyl myristate and mixtures thereof.

6. The transdermal drug delivery system according to claim 1, wherein said matrix layer further comprises 5 wt % or less of a gelling polymer which is selected from the group consisting of hydroxypropyl cellulose, hydroxymethyl cellulose and carbomer.

7. The transdermal drug delivery system according to claim 1, wherein said backing film is a non-woven fabric or film comprising polymer substrates selected from the group consisting of polyurethanes, polyesters, polyethylenes and rayon.

8. A process of making a transdermal drug delivery system for an anti-inflammatory analgesic agent comprising the steps of forming two adhesive layers by applying an adhesion solution comprising diclofenac diethylammonium, a non-aqueous acrylic polymer adhesive and a non-ionic surfactant onto one side of a backing film and a release liner respectively; drying said adhesive layers at a temperature range of 80~120° C. for 1 to 10 minutes; forming a volatile absorption enhancer layer by applying a solution comprising a terpene, a dissolution assistant and a gelling polymer onto one side of one of said adhesive layers and laminating the other adhesive layer on said volatile absorption enhancer layer such that said enhancer layer is sandwiched between the two adhesive layers.

9. A transdermal drug delivery system for an anti-inflammatory analgesic agent made from the process according claim 8.

* * * * *